United States Patent [19]

Monin et al.

[11] Patent Number: Plant 5,802

[45] Date of Patent: Nov. 18, 1986

[54] CHERRY ROOTSTOCK-GM 79 CULTIVAR

[75] Inventors: André Monin, Namur; Richard Trefois, Charleroi, both of Belgium

[73] Assignee: N.V. Jo Nicolai & Co., Duras, Belgium

[21] Appl. No.: 604,141

[22] Filed: Apr. 26, 1984

[51] Int. Cl. ..... A01H 5/00

[52] U.S. Cl. ..... Plt./37

[58] Field of Search ..... Plt./37

[56] References Cited

U.S. PATENT DOCUMENTS

P.P. 4,059 6/1977 Tydeman ..... Plt./37

P.P. 5,159 12/1983 Tydeman ..... Plt./37

*Primary Examiner*—James R. Feyrer

*Attorney, Agent, or Firm*—Cushman, Darby & Cushman

[57] ABSTRACT

A new and distinct cultivar of cherry tree useful as a dwarfing, small-leaved cherry rootstock substantially as shown and described, discovered in De Belder Nursery, Kalmthout, Belgium, growing among a population of *Prunus canescens,* which, when used as an understock, induces less growth of the cherry tree, is graft-compatible with most commercial cultivars of sweet cherry trees, and provides increased fruit production of the early life of the grafted cherry tree.

8 Drawing Figures

BACKGROUND OF THE INVENTION

This new and distinctive cultivar of cherry rootstock was first observed in De Belder Nursery, Kalmthout, Belgium in 1964, growing among a population of *Prunus canescens.*

It has since been vegetatively propagated at the same place both by herbaceous cutting under mist propagation, and by micropropagation in vitro.

In comparison with closely related species known under the name of "*Prunus canescens Bois*" of which there exists some forms having a fastigiate habit and other ones a drooping habit, the new cherry rootstock has a drooping canopy and the trees are smaller sized. The rootstock is further characterized by a tendency to vegetate multiplication, the ability to produce dwarfed plants after grafting, and good graft compatibility with commercial varieties of sweet cherries, these features having been demonstrated by ten years experience.

SUMMARY OF THE INVENTION

The new and distinct cultivar of cherry rootstock, *Prunus canescens,* which has been given the designation GM 79 in which the initial letters stand for Grand Manil, (the Belgian experimental station) is of a semi-weeping growing type, produces semi-dwarf trees, produces small leaves approximately 4.5 cm. in length, with a very acuminate apex, a length-to-width ratio greater than 2.1 to 1, with greatest width being under the middle of the leaf.

BRIEF DESCRIPTION OF THE DRAWINGS

The accompanying drawings show typical specimens of the new and distinct cultivar of cherry rootstock wherein.

DETAILED DESCRIPTION

Figure 1:
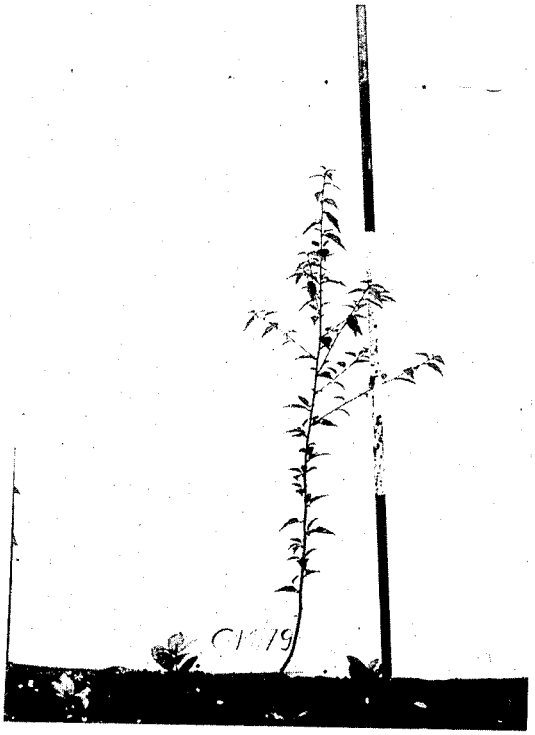
FIG. 1 shows a one year unbudded tree of the new cultivar of cherry rootstock.
Figure 2:
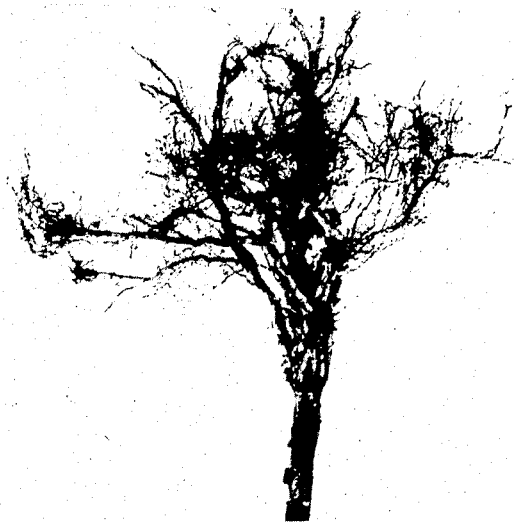
FIG. 2 shows the root system of such a one year tree.
Figure 3:
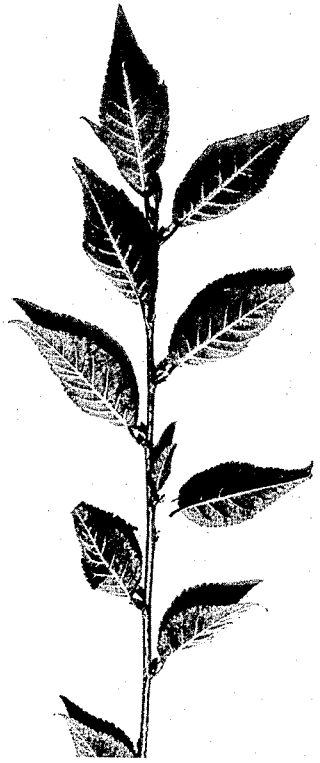
FIG. 3 shows a foliated bough of the new cultivar of cherry rootstock.
Figure 4:
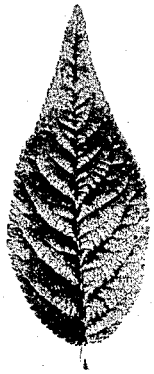
FIG. 4 shows the upper side of a leaf thereof.
Figure 5:
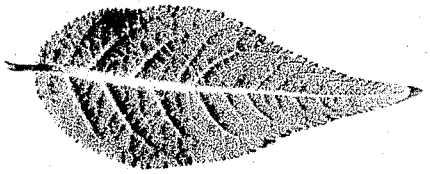
FIG. 5 shows the underside of a leaf thereof.
Figure 6:
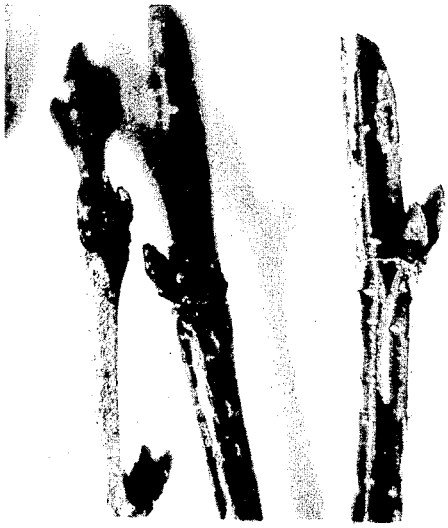
FIG. 6 shows details of buds thereof.
Figure 7:
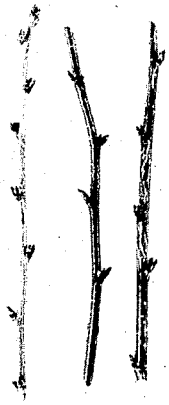
FIG. 7 shows segments of non-foliated boughs thereof.
Figure 8:
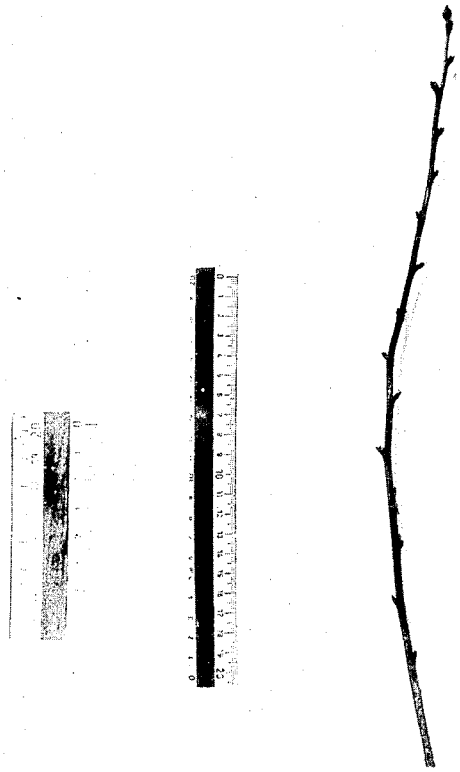
FIG. 8 shows an entire non-foliated bough thereof.

The new cultivar serves as a support for other cherry tree cultivars grafted thereon. (The inflorescence, fruit and seed of the new cultivar itself has not been systematically observed.) Accordingly the flowers, fruit and seed produced on the rootstock depend on the characteristics of the cherry tree cultivars which are grafted thereon.

The tree has a medium vigor and a drooping or semi-weeping habit. Current year's stem growth is villous, with pubescence increasing from the annual ring to the apex. The bottom color is gray-brown, with few small lenticels. The ultimate height and breadth of the grafted tree is about 4.5-about 5.0 meters.

The leaf is petiolate and sharp pointed (30°); the symmetrical base is rounded off. The color of the leaf is dark green and the same is lustreless. The upper and lower faces are slightly pubescent; the venation on the inferior face is more villous. The leaf venation is pennate; the ribs reach the edge of the leaf. The ratio length of the leaf to length of stalk is higher than 4.3/1. The margin of the leaf is double serrate (every other tooth is longer) with, on each tooth, a small violet-colored gland. The pubescent petiole generally shows 2 to 4 violet-colored glands. The base of the leaf petiole often shows one-half centimeter toothed stipules which are as long as the petiole itself. The internodes of the twig are small (±24 mm) at least when taken from a one year bough.

The buds: The apex contents several buds among which is found one central vegetative bud surrounded by 3–4 flower buds. The upper halves of the twigs show groups of 3 buds, the central one being vegetative and the two lateral being flower buds. In the lower parts of the twigs, the buds are isolated or grouped by twos. In such lower parts, flowers are scarce. The auxiliary buds are always detached from the twigs. Leaf scale scars are protruding and triangular. The surface of the scar is smaller than the base of the bud.

Physiology of GM 79

Vigor: Medium.

Budding takes place in the middle spring in Belgium.

Flowering takes two to four weeks after budding.

Growth of the twigs is fast at the beginning, foliation is quickly developed in spring.

Leaffall is half late.

This rootstock is well graft-compatible with most commercial cultivars of sweet cherry trees. The grafted plant has a medium vigorous growth, which may vary according to the soil conditions; fruits are observed early; many bunches appear as soon as the fruit-bearing wood is three years old. (Sweet cherry fertile cultivars VAN And BURLAT, when grafted on GM 79 produce trees that are about one-half to about two-thirds the size of controls produced by equivalent grafts of the same cultivars on rootstock of *Prunus Avium* (F12/1). Fruit-setting of the grafts on M79 is very precocious, e.g. 3–4 years after grafting, compared with 6–8 years for the controls.)

The colors of the plant parts of GM 79 have not been observed to distinguish the new cultivar from the species per se.

Propagation

By herbaceous cutting under mist propagation and by micropropagation in vitro; the roots are creeping.

This rootstock throws out suckers, but no more than the standard plant F 12/1 (reference of the East Malling Station).

The rootstock is made healthier against virus by cultivation in vitro, the so-propagated mericlone being F 4245 (references from the "Station des cultures fruitieres et maraicheres in Gembloux (Belgium)".

The behavior in nursery is good.

We claim:

1. A new and distinct cultivar of cherry tree useful as a dwarfing, small-leaved cherry rootstock substantially as shown and described, discovered in De Belder Nursery, Kalmthout, Belgium, growing among a population of *Prunus canescens,* which, when used as an understock, induces less growth of the cherry tree, is graft-compatible with most commercial cultivars of sweet cherry trees, and provides increased fruit production of the early life of the grafted cherry tree.

* * * * *